US011000327B2

(12) United States Patent
Schlotterback et al.

(10) Patent No.: US 11,000,327 B2
(45) Date of Patent: May 11, 2021

(54) BONE DEFECT REPAIR APPARATUS AND METHOD

(71) Applicant: NEXTREMITY SOLUTIONS, INC., Warsaw, IN (US)

(72) Inventors: Ryan Schlotterback, Warsaw, IN (US); Greg Denham, Warsaw, IN (US); John Pepper, Warsaw, IN (US)

(73) Assignee: NEXTREMITY SOLUTIONS, INC., Warsaw, IN (US)

( * ) Notice: Subject to any disclaimer, the term of this patent is extended or adjusted under 35 U.S.C. 154(b) by 209 days.

(21) Appl. No.: 16/221,036

(22) Filed: Dec. 14, 2018

(65) Prior Publication Data
US 2020/0188003 A1 Jun. 18, 2020

(51) Int. Cl.
*A61B 17/88* (2006.01)
*A61B 17/86* (2006.01)
(Continued)

(52) U.S. Cl.
CPC ...... *A61B 17/8872* (2013.01); *A61B 17/8625* (2013.01); *A61B 17/1775* (2016.11);
(Continued)

(58) Field of Classification Search
CPC . A61B 17/17; A61B 17/1739; A61B 17/1775; A61B 17/68; A61B 2017/564; A61B 2017/565; A61B 2017/681
See application file for complete search history.

(56) References Cited

U.S. PATENT DOCUMENTS

| 2,614,559 A | 10/1952 | Livingston |
| 4,016,874 A | 4/1977 | Maffei |

(Continued)

FOREIGN PATENT DOCUMENTS

| WO | 2006091460 A1 | 8/2006 |
| WO | 2007138062 A1 | 12/2007 |

(Continued)

OTHER PUBLICATIONS

International Preliminary Report on Patentability for PCT Application No. PCT/US2012/022723, dated Aug. 8, 2013.
(Continued)

*Primary Examiner* — Eric S Gibson
(74) *Attorney, Agent, or Firm* — Heslin Rothenberg Farley & Mesiti P.C.; Victor A. Cardona, Esq.

(57) ABSTRACT

An orthopedic instrument assembly for placing an implant into a medial cuneiform of a foot, the assembly includes a targeting guide having a body with an elongated linear base. A threaded rack is disposed along the elongated linear base. A compression-distraction frame pre-compresses the joint prior to placement of a joint fixation element. The compression-distraction frame is translatably connected to the rack of the guide body base. The compression-distraction frame is releasably, statically connectable to a first metatarsal bone and a post. The post has a generally cylindrical shape and a longitudinal axis, and has a plurality of threaded cylindrical bores disposed therethrough at predefined angles relative to the longitudinal axis. The post is releasably, statically connectable to the targeting guide.

18 Claims, 21 Drawing Sheets

(51) Int. Cl.
  *A61B 17/56* (2006.01)
  *A61B 17/90* (2006.01)
  *A61B 17/84* (2006.01)
  *A61B 17/17* (2006.01)
  *A61B 17/68* (2006.01)
  *A61B 90/00* (2016.01)

(52) U.S. Cl.
  CPC ......... *A61B 17/848* (2013.01); *A61B 17/8875* (2013.01); *A61B 2017/565* (2013.01); *A61B 2017/681* (2013.01); *A61B 2017/90* (2013.01); *A61B 2090/062* (2016.02)

(56) References Cited

U.S. PATENT DOCUMENTS

| | | | |
|---|---|---|---|
| 4,541,424 A | 9/1985 | Grosse | |
| 4,622,959 A | 11/1986 | Marcus | |
| 5,295,991 A | 3/1994 | Frigg | |
| 5,411,504 A | 5/1995 | Vilas | |
| 5,474,561 A | 12/1995 | Yao | |
| 5,480,402 A | 1/1996 | Kim | |
| 6,030,391 A * | 2/2000 | Brainard | A61B 17/15 606/82 |
| 6,093,192 A | 7/2000 | Abel | |
| 6,210,414 B1 | 4/2001 | Lin | |
| 6,517,541 B1 | 2/2003 | Sesic | |
| 6,579,293 B1 | 6/2003 | Chandran | |
| 6,620,195 B2 | 9/2003 | Goble | |
| 7,169,149 B1 | 1/2007 | Hajianpour | |
| 7,179,259 B1 | 2/2007 | Gibbs | |
| 7,311,710 B2 | 12/2007 | Zander | |
| 7,713,291 B2 | 5/2010 | Vaughan | |
| 8,034,056 B2 | 10/2011 | Fencl | |
| 8,157,803 B1 | 4/2012 | Zirkle, Jr. | |
| 8,187,281 B2 | 5/2012 | Cresina et al. | |
| 8,257,361 B2 * | 9/2012 | Ritchey | A61B 17/72 606/96 |
| 8,303,589 B2 | 11/2012 | Tyber et al. | |
| 8,313,487 B2 | 11/2012 | Tyber et al. | |
| 8,328,806 B2 | 12/2012 | Tyber et al. | |
| 8,343,199 B2 | 1/2013 | Tyber et al. | |
| 8,468,071 B2 | 6/2013 | Rau et al. | |
| 8,679,119 B2 | 3/2014 | Lopez-Oliva Munoz | |
| 8,821,546 B2 | 9/2014 | Vaughan | |
| 8,900,274 B2 | 12/2014 | Tyber et al. | |
| 8,920,453 B2 | 12/2014 | Tyber et al. | |
| 8,920,476 B2 | 12/2014 | Tyber et al. | |
| D722,380 S | 2/2015 | Palmer | |
| 9,017,329 B2 | 4/2015 | Tyber et al. | |
| 9,044,282 B2 | 6/2015 | Tyber et al. | |
| 9,107,709 B2 | 8/2015 | Wieland et al. | |
| 9,289,220 B2 | 3/2016 | Wolfe et al. | |
| 9,364,271 B2 | 6/2016 | Tyber et al. | |
| 9,421,103 B2 | 8/2016 | Jeng et al. | |
| 9,603,640 B2 | 3/2017 | Palmer et al. | |
| 9,615,870 B2 | 4/2017 | Tyber et al. | |
| 9,622,805 B2 * | 4/2017 | Santrock | A61B 17/1682 |
| 9,662,221 B2 * | 5/2017 | Surma | A61B 17/8645 |
| 9,814,474 B2 | 11/2017 | Montoya et al. | |
| 9,877,752 B2 | 1/2018 | Tyber et al. | |
| 9,907,562 B2 * | 3/2018 | DaCosta | A61B 17/1725 |
| 9,936,994 B2 | 4/2018 | Smith et al. | |
| 9,936,995 B2 | 4/2018 | Dacosta et al. | |
| 9,943,347 B2 | 4/2018 | Wayne et al. | |
| 10,045,807 B2 | 8/2018 | Santrock et al. | |
| 10,327,829 B2 | 6/2019 | Dacosta et al. | |
| 10,335,220 B2 | 7/2019 | Smith et al. | |
| 10,342,590 B2 * | 7/2019 | Bays | A61B 17/152 |
| 10,390,844 B2 | 8/2019 | Wieland et al. | |
| 10,849,670 B2 * | 12/2020 | Santrock | A61B 17/15 |
| 2003/0073999 A1 | 4/2003 | Putnam | |
| 2003/0135216 A1 | 7/2003 | Sevrain | |
| 2005/0055023 A1 | 3/2005 | Sohngen | |
| 2005/0107791 A1 | 5/2005 | Manderson | |
| 2005/0283154 A1 | 12/2005 | Orbay | |
| 2006/0015123 A1 | 1/2006 | Fencl | |
| 2006/0122600 A1 | 6/2006 | Cole | |
| 2008/0077132 A1 | 3/2008 | Medoff | |
| 2008/0147066 A1 | 6/2008 | Longsworth | |
| 2009/0036931 A1 * | 2/2009 | Pech | A61B 17/1775 606/280 |
| 2009/0149861 A1 * | 6/2009 | Brodsky | A61B 17/1725 606/96 |
| 2009/0157077 A1 | 6/2009 | Larsen | |
| 2009/0292292 A1 | 11/2009 | Fencl | |
| 2010/0036440 A1 | 2/2010 | Morris | |
| 2010/0114315 A1 | 5/2010 | Manderson | |
| 2011/0125153 A1 | 5/2011 | Tyber et al. | |
| 2011/0160728 A1 | 6/2011 | Blitz et al. | |
| 2011/0230884 A1 | 9/2011 | Mantzaris et al. | |
| 2011/0245885 A1 * | 10/2011 | Powell | A61B 17/1725 606/86 R |
| 2012/0095560 A1 * | 4/2012 | Donner | A61B 17/1626 623/17.11 |
| 2012/0277745 A1 * | 11/2012 | Lizee | A61B 17/1739 606/59 |
| 2012/0330313 A1 | 12/2012 | Grady | |
| 2013/0030446 A1 * | 1/2013 | Wayne | A61B 17/1717 606/104 |
| 2013/0245626 A1 | 9/2013 | Lavi | |
| 2013/0325006 A1 | 12/2013 | Michelinie | |
| 2014/0243827 A1 | 8/2014 | Boileau | |
| 2015/0032168 A1 * | 1/2015 | Orsak | A61B 17/1775 606/304 |
| 2015/0173811 A1 | 6/2015 | Tyber et al. | |
| 2015/0265323 A1 | 9/2015 | Sems | |
| 2016/0354128 A1 | 12/2016 | Jeng et al. | |
| 2017/0164989 A1 * | 6/2017 | Weiner | A61B 17/1682 |
| 2017/0216043 A1 * | 8/2017 | Surma | A61F 2/42 |
| 2018/0161079 A1 | 6/2018 | Tyber et al. | |
| 2018/0193039 A1 * | 7/2018 | Dacosta | A61B 17/72 |
| 2018/0242937 A1 | 8/2018 | Lintula et al. | |
| 2018/0242988 A1 * | 8/2018 | Dacosta | A61B 17/1728 |
| 2018/0280069 A1 | 10/2018 | Barmes et al. | |
| 2018/0289379 A1 | 10/2018 | Dacosta et al. | |
| 2018/0317992 A1 | 11/2018 | Santrock et al. | |
| 2019/0117238 A1 * | 4/2019 | Levitt | A61B 17/171 |
| 2019/0125418 A1 * | 5/2019 | Muller | A61B 17/1725 |
| 2019/0274745 A1 * | 9/2019 | Smith | A61B 17/1775 |
| 2019/0307498 A1 | 10/2019 | Dacosta et al. | |
| 2019/0328436 A1 | 10/2019 | Bays et al. | |
| 2020/0188003 A1 * | 6/2020 | Schlotterback | A61B 17/8625 |
| 2020/0253641 A1 * | 8/2020 | Treace | A61B 17/151 |
| 2020/0281637 A1 * | 9/2020 | Denham | A61B 17/8875 |

FOREIGN PATENT DOCUMENTS

| | | |
|---|---|---|
| WO | 2010033702 A2 | 3/2010 |
| WO | 2018/157168 A1 | 8/2018 |
| WO | 2018/157170 A1 | 8/2018 |
| WO | 2018/183875 A1 | 10/2018 |
| WO | 2018/183884 A2 | 10/2018 |
| WO | 2018/202782 A2 | 11/2018 |
| WO | 2019/027821 A1 | 2/2019 |

OTHER PUBLICATIONS

International Search Report for PCT/US2012/022723 dated Jul. 6, 2012.
International Preliminary Report on Patentability for PCT Application No. PCT/US2012/022755, dated Aug. 8, 2013.
International Search Report for PCT/US2012/022755 dated Jul. 6, 2012.

* cited by examiner

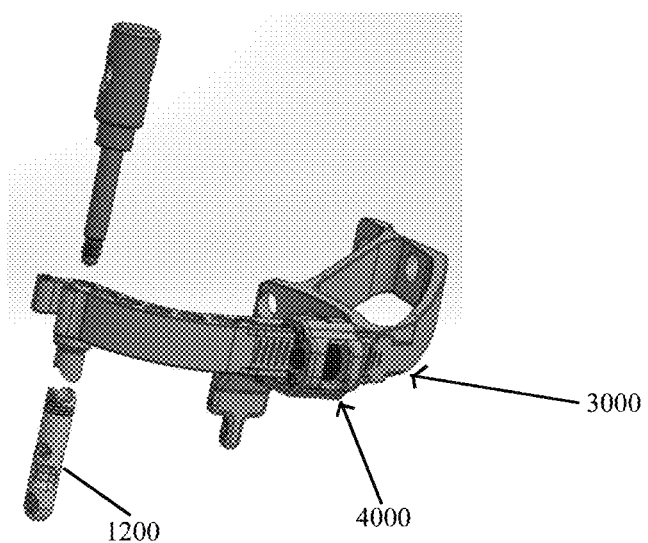
FIG. 8
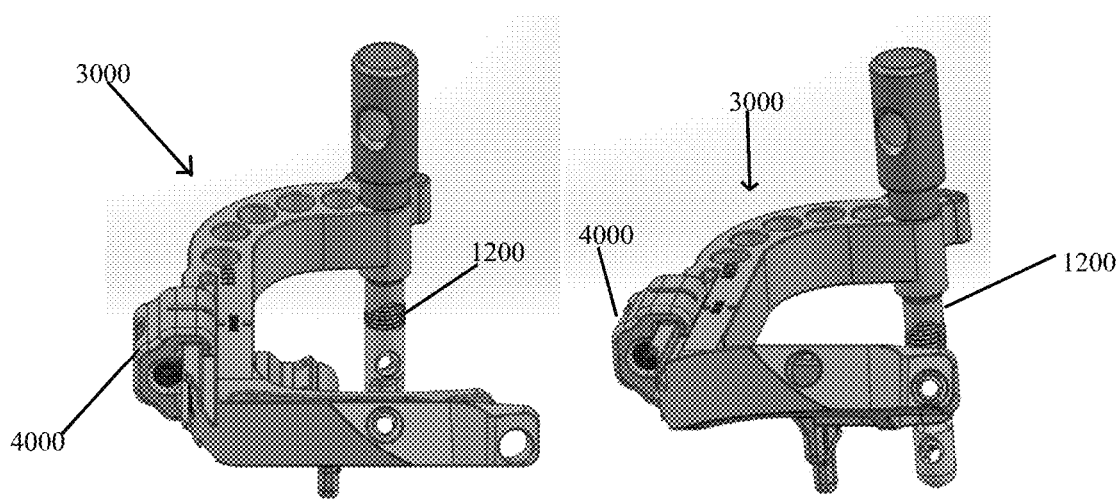
FIG. 9
FIG. 10

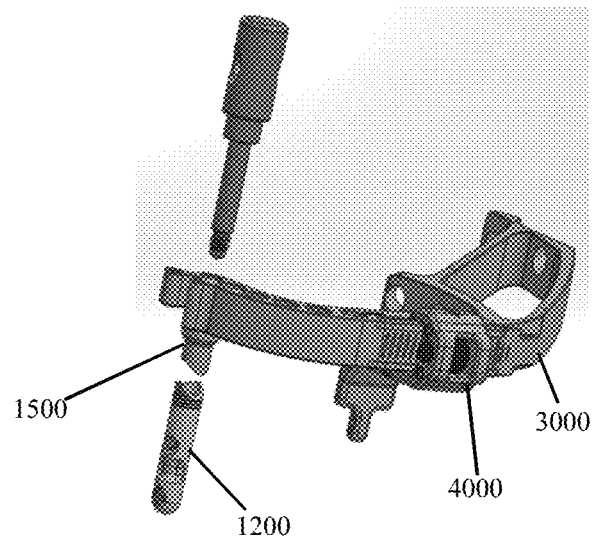 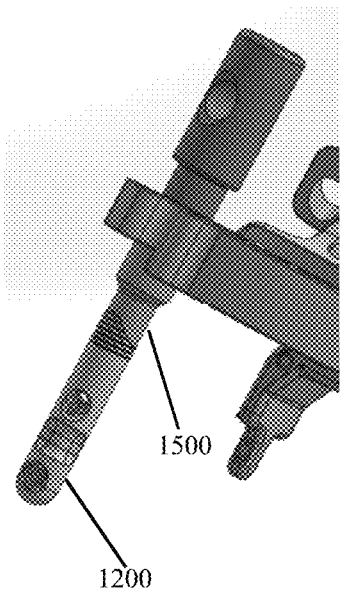
FIG. 15      FIG. 16
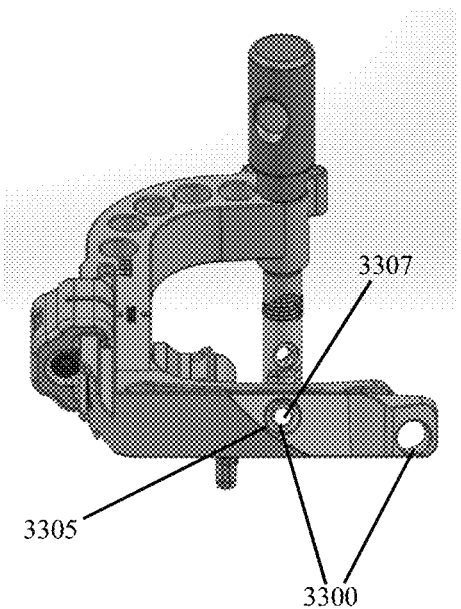 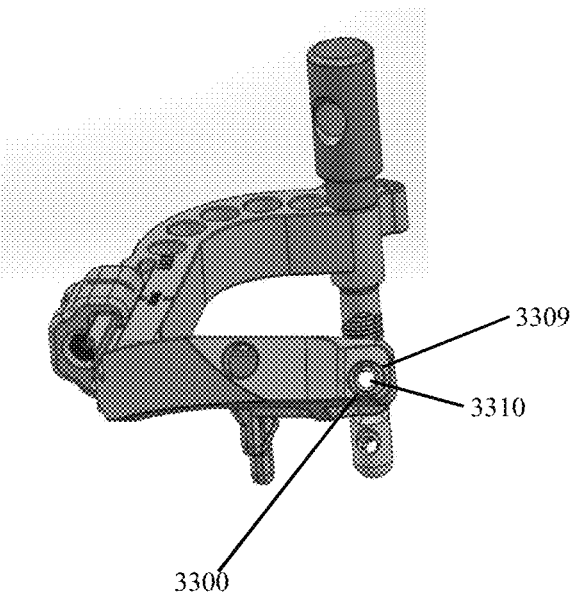
FIG. 17      FIG. 18

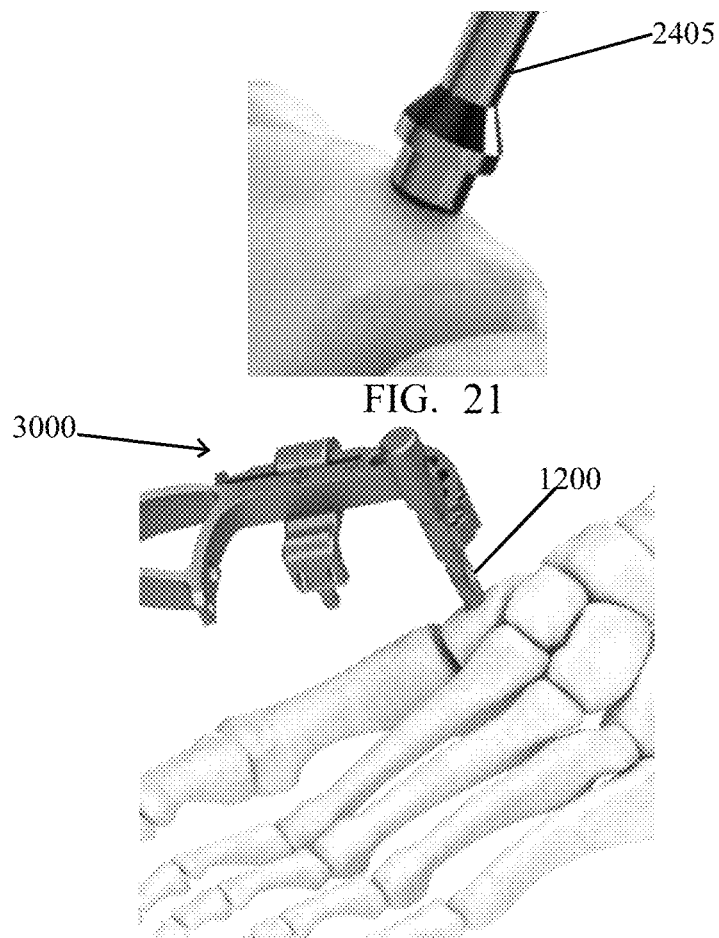
FIG. 21
FIG. 22
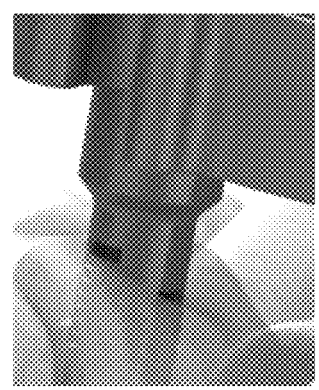
FIG. 23

BONE DEFECT REPAIR APPARATUS AND METHOD

CROSS-REFERENCE TO RELATED APPLICATIONS

This application is related to U.S. Pat. No. 9,603,640, Ser. No. 13/982,152, entitled "Lower Extremity Fusion Devices and Methods", U.S. Pat. No. 9,662,221, Ser. No. 13/982,124, entitled "Upper Extremity Fusion Devices and Methods, and U.S. Patent No. 2017/0216043, Ser. No. 15,488,903, entitled "Upper Extremity Fusion Devices and Methods", the entire disclosures of which are incorporated herein by reference.

BACKGROUND

Field of the Invention

This application relates to apparatuses, devices, and methods for joining bones.

Description of the Related Art

Hallux valgus is the medical term for a bunion. The first tarsal-metatarsal (TMT) joint is an important joint at the inner part of the middle of the foot. The two bones that meet to form this joint are the first metatarsal and medial cuneiform bones. When this joint has too much looseness or movement, the condition is known as hypermobility or instability. When this joint becomes hypermobile, the first metatarsal moves too much in one direction and the first toe compensates by moving too much in the other direction. When this happens, a bunion develops.

The Lapidus procedure is a type of fusion of the first TMT joint that decreases the movement of that joint and straightens out the first metatarsal and toe. So the Lapidus procedure treats bunions caused by first TMT joint hypermobility.

The goal of the Lapidus procedure is to surgically treat hallux valgus that is caused by first TMT joint hypermobility. An orthopaedic foot and ankle surgeon realigns to a normal toe shape by placing the first metatarsal straight with the medial cuneiform bone and locking or fusing these two bones together. When the first TMT joint is fused, the first metatarsal will not move abnormally. This will allow the first toe to stay straight and prevent the bunion from coming back.

Hammertoe deformity, the most common deformity of the lesser toes, is a flexion deformity of the proximal interphalangeal (PIP) joint of the toe, with hyperextension of the metatarsophalangeal (MTP) and distal interphalangeal (DIP) joints. Progressive PIP joint flexion deformity typically leads to compensatory hyperextension of the MTP and DIP joints. This makes the PIP joint prominent dorsally. Pain occurs due to rubbing of the prominence against the patient's shoe. The deformity is flexible at first but usually becomes fixed over time. When the deformity is flexible, various procedures can be utilized that involve manipulation of the involved tendons. However, when the deformity is fixed, PIP fusion or joint replacement is often required. Implants available for this purpose include the Weil-Carver™ Hammertoe Implant (Biomet®, Inc., Warsaw, Ind.), Flexible Digital Implant (Tornier, Inc. Edina, Minn.), SHIP Implant (Sgarlato Labs, Campbell Calif.), Digital Compression Screw (BioPro®, Port Huron Mich.), Smart Toe™ Intramedullary Memory Implant (Memometal Inc., Memphis Tenn.) and StayFuse™ Intramedullary Fusion Device (Tornier, Inc. Edina, Minn.). The latter three implants are used when fusion is desired, since the other implants allow some flexibility of the joint. With all current implants, placement is critical because, when mounted, there is no adjustability in the angle of flexion between the two cut bones to be joined.

There is thus a need for alternative designs for implants for joining two bone pieces, including implants that fix the two bone pieces, particularly designs that allow adjustment of the angle of flexion between the two bones. The present invention addresses that need.

SUMMARY

In one exemplary embodiment, the present invention includes a post for use with a targeting guide and configured to anchor into a bone, the post having a generally cylindrical shape and a longitudinal axis, the post having a plurality of threaded cylindrical bores disposed through the post at predefined angles relative to the longitudinal axis, the post releasably, statically connectable to a targeting guide such that the targeting guide and the post may rotate around the longitudinal axis, the post having a plug releasably connected to the post.

In another exemplary embodiment, the present invention includes a post guide for use with an orthopedic surgery instrument set for placing an implant into the medial cuneiform of the foot, the post guide has a body, a first paddle extending from the body and having a first size and, the first paddle insertable between a medial cuneiform and a first metatarsal of a human foot, a second paddle extending from the body and insertable between the medial cuneiform and a second metatarsal of the foot, the second paddle having a size differing from the size of the first paddle, the body having a bore disposed through the body, the bore adapted to receive a k-wire.

In another exemplary embodiment, the present invention includes an orthopedic instrument assembly for placing an implant into the medial cuneiform of the foot, the assembly comprising: a targeting guide, the targeting guide comprising a body having an elongated linear base, a threaded rack disposed along the elongated linear base, a compression-distraction frame for pre-compressing the joint prior to placement of a joint fixation element, the compression-distraction frame translatably connected to the rack of the guide body base, the compression-distraction frame further releasably, statically connectable a first metatarsal bone, a post, the post having a generally cylindrical shape and a longitudinal axis, the post comprising a plurality of threaded cylindrical bores disposed through the post at predefined angles relative to the longitudinal axis, the post releasably, statically connectable to the targeting guide such that the targeting guide and the post may rotate around the longitudinal axis, the post having a plug releasably connected to the post, the post disposed through the targeting guide and releasably connected to a second metatarsal bone wherein the second metatarsal bone is adjacent to the first metatarsal bone.

In another exemplary embodiment, the present invention may further comprise a depth probe configured to measure the distance between the surface of a bone and the back of the targeting guide to provide surgeons the ideal length of screw to use wherein the distal tip of the depth probe is configured to be more acute than the surface of the bone with respect to the long axis of the depth probe by remaining in contact with the most proximal aspect of a drilled hole and rotating with pressure applied to the grasping end of the depth probe.

BRIEF DESCRIPTION OF THE DRAWINGS

The present invention will be understood more fully from the detailed description given hereinafter and from the accompanying drawings of the preferred embodiment of the present invention, which, however, should not be taken to limit the invention, but are for explanation and understanding only.

In the drawings:

FIG. 8 shows a disassembled view of a targeting guide and post in accordance with the present invention.

FIG. 9 shows an assembled view of a targeting guide and post in accordance with the present invention.

FIG. 10 shows an assembled view of a targeting guide and post in accordance with the present invention.

FIG. 11 shows a reamer over the k-wire of FIG. 10.

FIG. 15 shows the targeting guide, implant post, and implant post fastener of FIG. 8.

FIG. 16 shows the targeting guide, implant post, and implant post fastener of FIG. 15 with the post engaged with the fastener.

FIG. 17 shows the targeting guide, implant post, and implant post fastener of FIG. 15 with a hole of the targeting guide aligning with a hole of the post.

FIG. 18 shows the targeting guide, implant post, and implant post fastener of FIG. 17 with different holes of the targeting guide post aligned.

FIG. 21 shows a close-up view of a reamer over the k-wire of FIG. 20.

FIG. 22 shows a targeting guide and implant post assembly of FIG. 18 with the post received in a reamed hole in the bone.

FIG. 23 shows a close-up view of the post received in the bone of FIG. 22.

Corresponding reference characters indicate corresponding parts throughout the several views. The exemplary embodiments set forth herein are not to be construed as limiting the scope of the invention in any manner.

DETAILED DESCRIPTION OF THE EMBODIMENTS

The present invention will be discussed hereinafter in detail in terms of various exemplary embodiments according to the present invention with reference to the accompanying drawings. In the following detailed description, numerous specific details are set forth in order to provide a thorough understanding of the present invention. It will be obvious, however, to those skilled in the art that the present invention may be practiced without these specific details. In other instances, well-known structures are not shown in detail in order to avoid unnecessary obscuring of the present invention.

Thus, all of the implementations described below are exemplary implementations provided to enable persons skilled in the art to make or use the embodiments of the disclosure and are not intended to limit the scope of the disclosure, which is defined by the claims. As used herein, the word "exemplary" or "illustrative" means "serving as an example, instance, or illustration." Any implementation described herein as "exemplary" or "illustrative" is not necessarily to be construed as preferred or advantageous over other implementations. Moreover, in the present description, the terms "upper", "lower", "left", "rear", "right", "front", "vertical", "horizontal", and derivatives thereof shall relate to the invention as oriented in FIG. 1.

Furthermore, there is no intention to be bound by any expressed or implied theory presented in the preceding technical field, background, brief summary or the following detailed description. It is also to be understood that the specific devices and processes illustrated in the attached drawings, and described in the following specification, are simply exemplary embodiments of the inventive concepts defined in the appended claims. Hence, specific dimensions and other physical characteristics relating to the embodiments disclosed herein are not to be considered as limiting, unless the claims expressly state otherwise.

Figure 1:
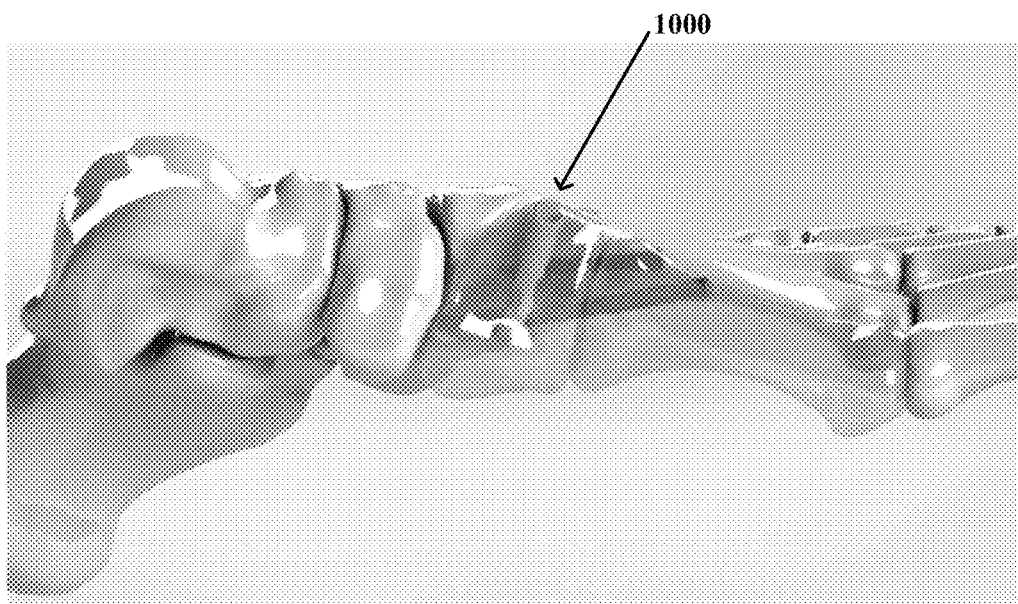
FIG. 1 shows an implant for use with the present invention inserted into a bone.

As depicted in FIG. 1, an orthopedic device 1000 is implanted into a human foot to correct a deformity. As will be described below, the present invention comprises surgical instruments and methods for properly placing implant 1000 into a medial cuneiform of the human foot in a manner that maximizes the amount of bone surrounding the implant by targeting the major axis of the cross section of the bone.

Figure 2:
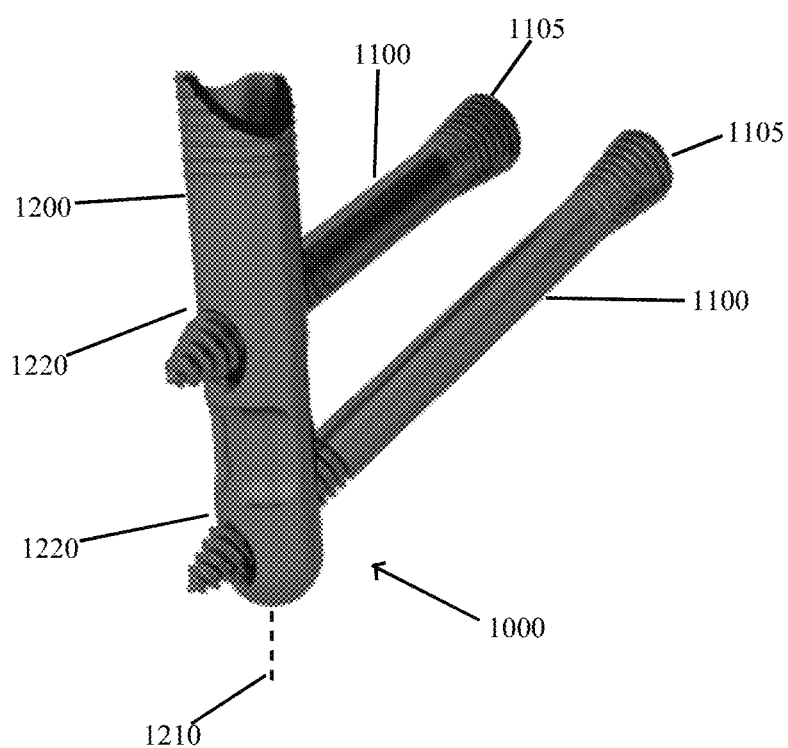
FIG. 2 shows an implant for use with the present invention.

Referring now to FIGS. 1 and 2, implant 1000 includes two or more solid shafted screws 1100. "Solid shafted" means that the portion of the screw that crosses the joint is not threaded and is at the major diameter of the distal screw thread. Screws 1100 cross the medial cuneiform/first metatarsal joint and lock into a post 1200. Locking screws 1100 into post 1200 requires seating the screws 1100 to a terminal thread thereof into post 1200 such that the posts have reached an end of potential advancement. In such a locked state, screws 1100 cannot move (translate or rotate) with respect to post 1200 or each other. Preferably, post 1200 has a diameter of 1.5 to 2.5 times a diameter of screws 1100. Heads 1105 of the screws 1100 are substantially tapered, "headless screws," allowing them to be seated further into bone than a headed screw.

Referring again to FIG. 2, implant post 1200 of implant 1000 comprises a substantially cylindrical shape having a longitudinal axis 1210 and threaded holes 1220 at predefined angles relative to the longitudinal axis 1210 of post 1200. Post 1200 is configured to be releasably connected (eliminating rotation and translation with respect to) to a targeting guide 3000 (FIG. 8) that directs instrumentation to the threaded holes 1220. For example, targeting guide 3000 may be releasable from the post by removing a post fastener. The post may also be configured to receive a post plug to prevent bone growth into connection threads of the post (i.e., to allow easy removal).

Figure 3:
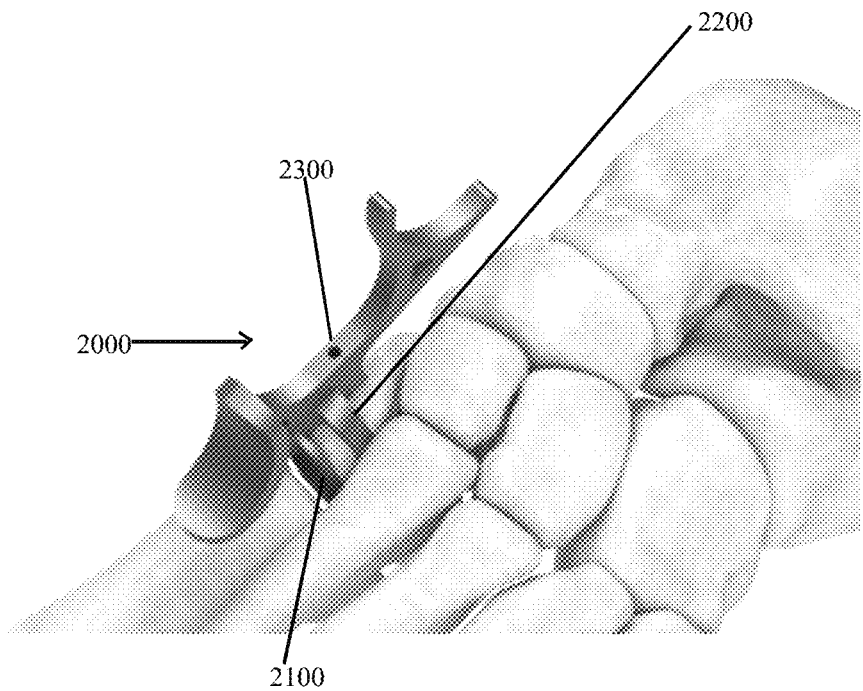
FIG. 3 shows an implant post drill guide in accordance with the present invention.
Figure 4:
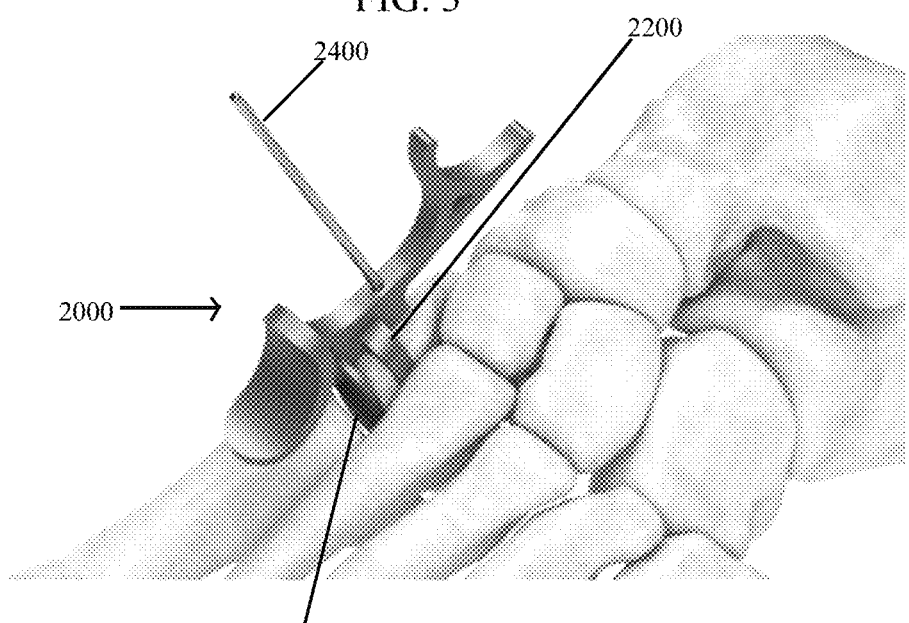
FIG. 4 shows a k-wire disposed through the post drill guide and bone of FIG. 3.

Referring to FIGS. 3-4, a post drill guide 2000 for post 1200 includes positioning paddles 2100 and 2200 respectively locatable in an articular space between a medial cuneiform and a first metatarsal of the foot and in a space between a lateral side of the medial cuneiform and a superior surface of the medial cuneiform. Guide 2000 is configured to maximize an amount of bone surrounding implant post 1200 when post 1200 is implanted into the medial cuneiform of the foot by targeting the major axis of the cross section of the bone. The guide has positioning features (i.e., paddles 2100, 2200) located at the articular space between the medial cuneiform and the First Metatarsal, the lateral side of the medial cuneiform, and the superior surface of the medial cuneiform. Guide 2000 also contains a bore 2300 for receiving a k-wire 2400. The K-wire drill is used to confirm correct placement on X-ray, and as a guide for a reamer that created the appropriate bore for implant post 1200 to be placed as described below.

Figure 5:
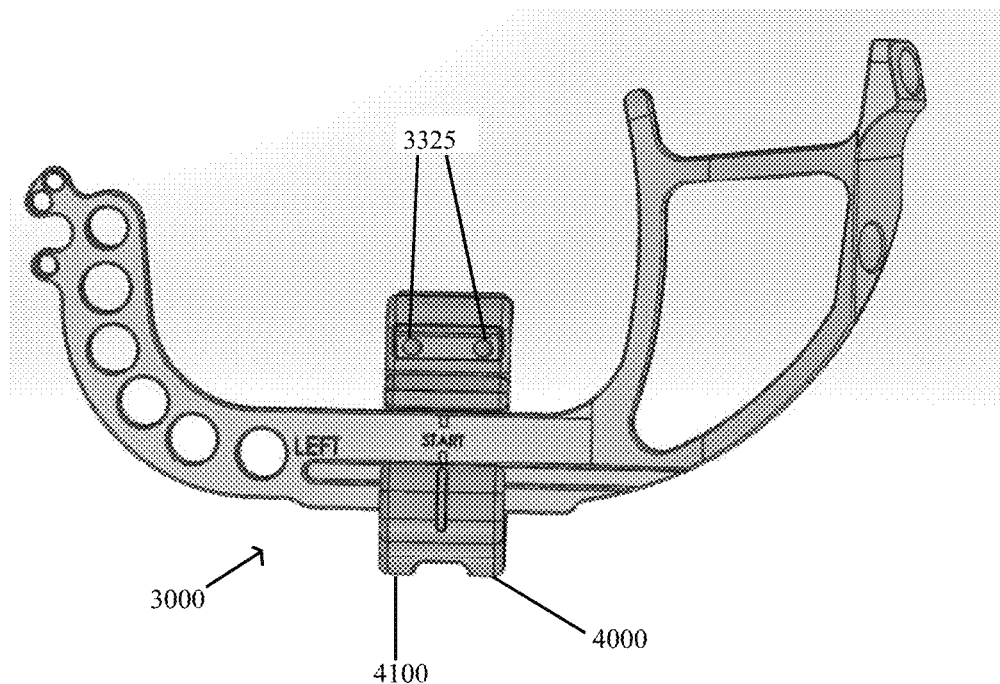
FIG. 5 shows a targeting guide and compression fixture in accordance with the present invention.

As depicted in FIG. 5, a targeting guide 3000 includes compression-distraction fixture 4000. Targeting guide 3000 contains a plurality of bores 3325 configured for a k-wire drill that directs placement of the k-wires in locations that do not interfere with screws 1100. Targeting guide 3000 may also rest against the metatarsal, aiding in the positioning of the guide, as well as the positioning of the first metatarsal.

Figure 6:
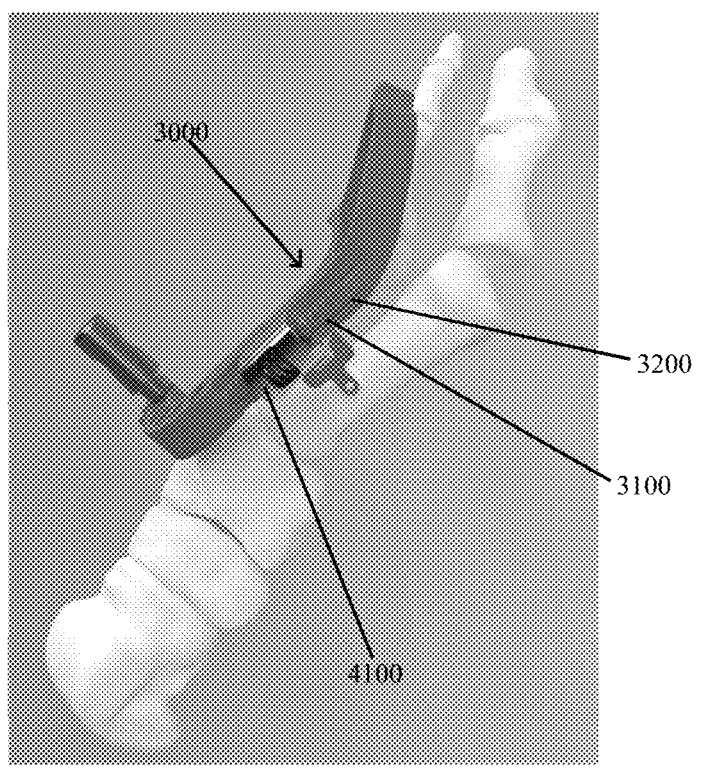
FIG. 6 shows another view of the assembly of FIG. 5.
Figure 7:
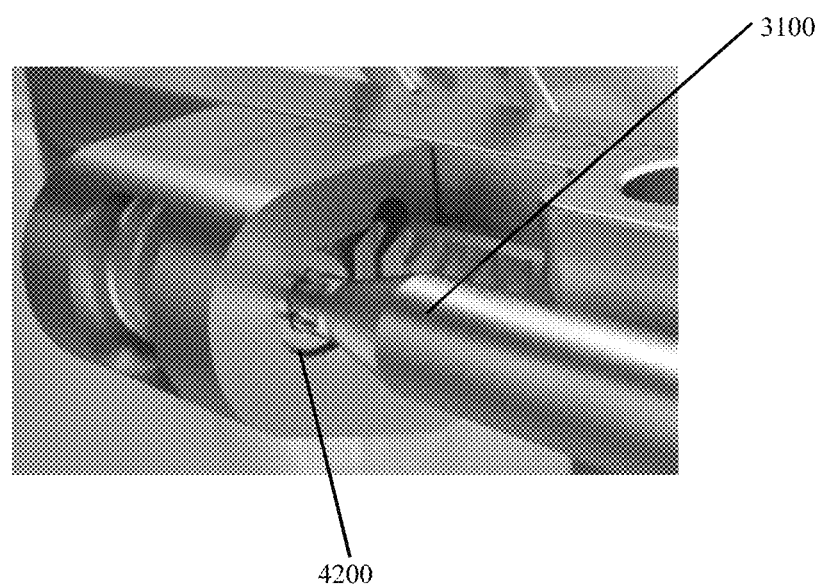
FIG. 7 shows another view of the assembly of FIG. 5.
Figure 11:
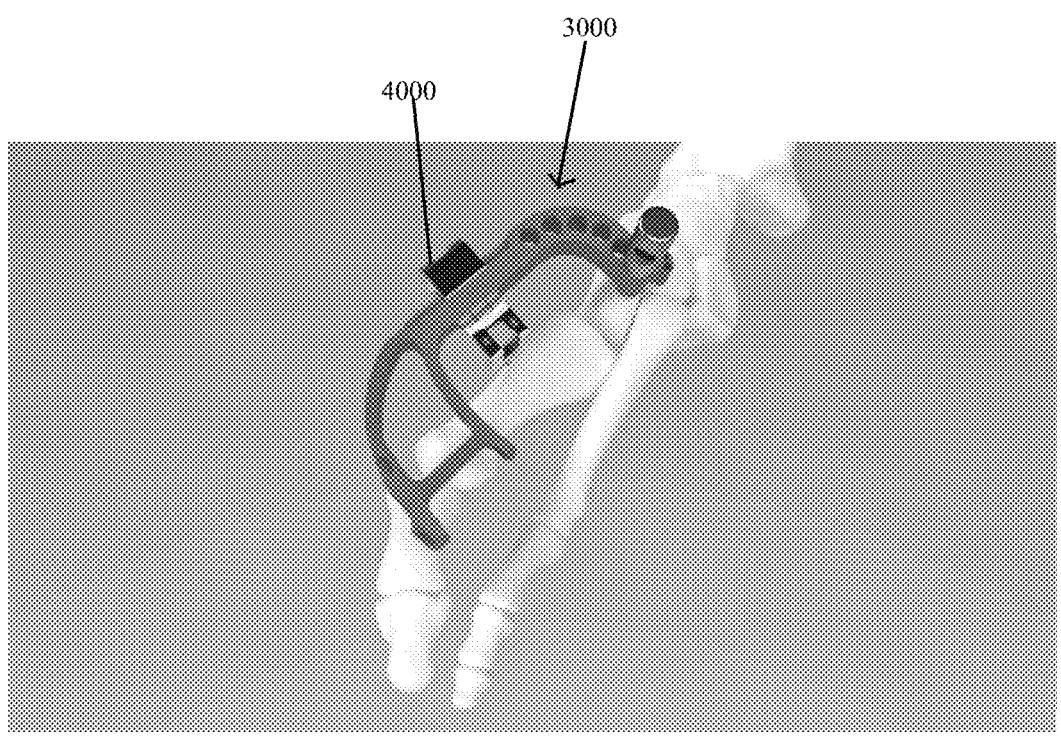
FIG. 11 shows an assembled view of a targeting guide and post rotating about the post in accordance with the present invention.

Referring now to FIGS. 5-7, compress-distraction fixture 4000 comprises a housing 4100 to hold a compression screw 4200 at a pitch that transmits rotational movement of the screw 4200 into translational movement of the housing 4100 by interfacing with a threaded rack 3100 of targeting guide 3000 and housing 4100 of compression distraction fixture 4000. As illustrated in FIG. 6, targeting guide 3000 comprises a linear base 3200 having a threaded rack 3100. Compression-distraction fixture 4000 is attached to rack 3100 such that compression-distraction fixture 4000 is movable along rack 3100 by actuating screw 4200 (FIG. 7) manipulated by a screwdriver, for example.

Referring to FIGS. 8-10, targeting guide 3000 is preferably pre-assembled to implant 1000. Advantageously, built-in compression-distraction fixture 4000 allows simplified joint preparation and pre-compression of the joint prior to placement of implant 1000. Targeting guide 3000 is preferably positioned substantially medial and dorsal to the bones being fused thereby reducing interference with X-ray imaging during procedure.

Figure 12:
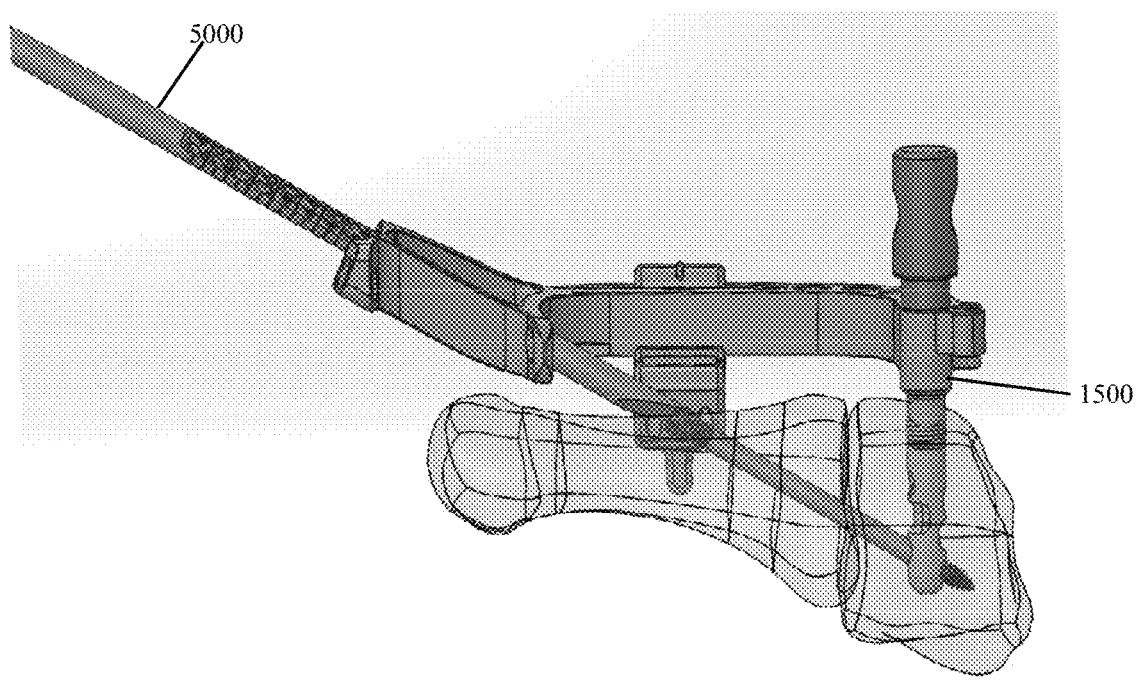
FIG. 12 shows a depth measuring probe in accordance with the present invention.

Referring generally to FIGS. 8-11, post 1200 and targeting guide 3000, when assembled, are rotatable around longitudinal axis 1210 (FIG. 2) of post 1200 when post 1200 is inserted in a bone to optimize a trajectory and a start location of implanted crossing screws 1100 with respect to the bone. Post 1200 is removably attached to targeting guide 3000 by a post fastener 1500 (FIG. 12). Post 1200 is further configured to receive a post plug 1400 (FIG. 36) to prevent bone growth into the connection threads of post 1200 for easy removal.

Figure 13:
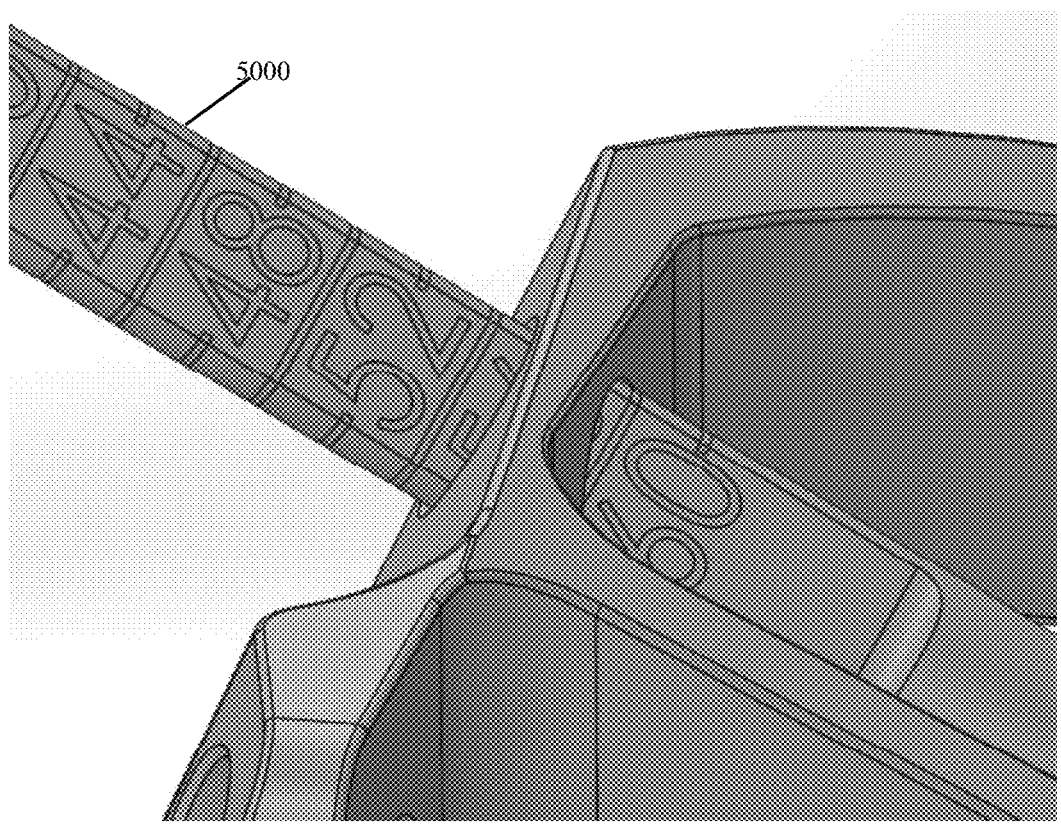
FIG. 13 shows a close-up view of FIG. 12.

Referring generally to FIGS. 12-13, an implant depth probe 5000 is configured to measure a distance between a surface of the bone and a back of targeting guide 3000 to provide surgeons an ideal length of screw 1100 to use. A distal tip of depth probe 5000 is configured to be more acute than the surface of the bone with respect to a long axis of depth probe 5000. Thus, the distal tip of depth probe 5000 always contacts the most proximal aspect of the drilled hole, and depth probe 5000 naturally rotates with pressure applied to a grasping end of depth probe 5000.

Figure 14:
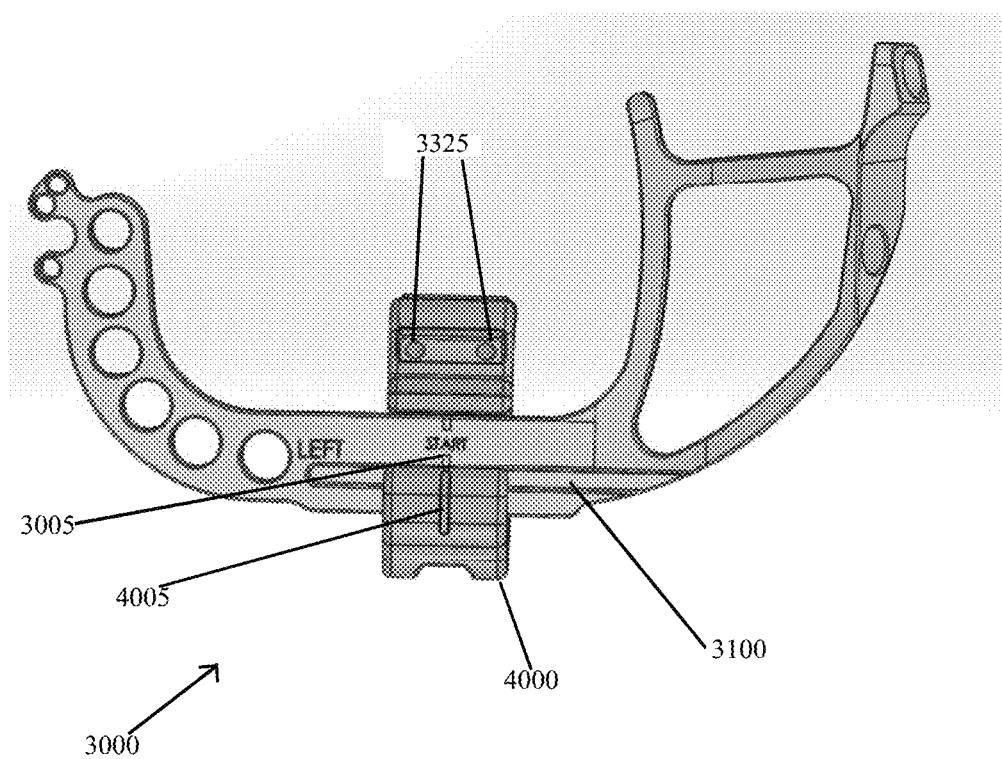
FIG. 14 shows the targeting guide of FIG. 5.

Referring now to FIG. 14, an exemplary surgical technique in accordance with the present invention for placing implant 1000 (FIG. 1) in bone begins with preparing instrumentation by first ensuring a top line 4005 of compression distraction fixture 4000 is aligned with a start line 3005 of targeting guide 3000. A screwdriver is used to rotate screw 4200, causing compression-distraction fixture 4000 to travel along rack 3100 of targeting guide 3000. Improper alignment may restrict potential distraction and compression travel of the compression-distraction fixture 4000.

Referring to FIGS. 15 and 16, implant post 1200 may be assembled to targeting guide 3000 by threading post fastener 1500 into implant post 1200, with targeting guide 3000 positioned between. After firm hand tightening of post fastener 1500, there should be no gap or play between the components.

Referring to FIGS. 17-18, siting holes 3300 may be located in targeting guide 3000, alignment can be visualized to ensure proper assembly and left/right foot selection. A medial hole 3305 of siting holes 3300 of the targeting guide may align with a plantar hole 3307 in post 1200 as depicted in FIG. 17. A lateral hole 3308 of siting holes 3300 of the targeting guide aligns with a dorsal hole 3310 of the post as depicted in FIG. 18. A surgeon may then perform soft tissue releases to ensure full mobility of a first metatarsal to a desired correction position and makes a dorsal incision over a tarsometatarsal joint.

Referring now to FIG. 3, post drill guide 2000 may be positioned so that largest paddle 2100 is between the medial cuneiform and the first metatarsal and smaller paddle 2200 is between the medial cuneiform and the second metatarsal.

Figure 19:
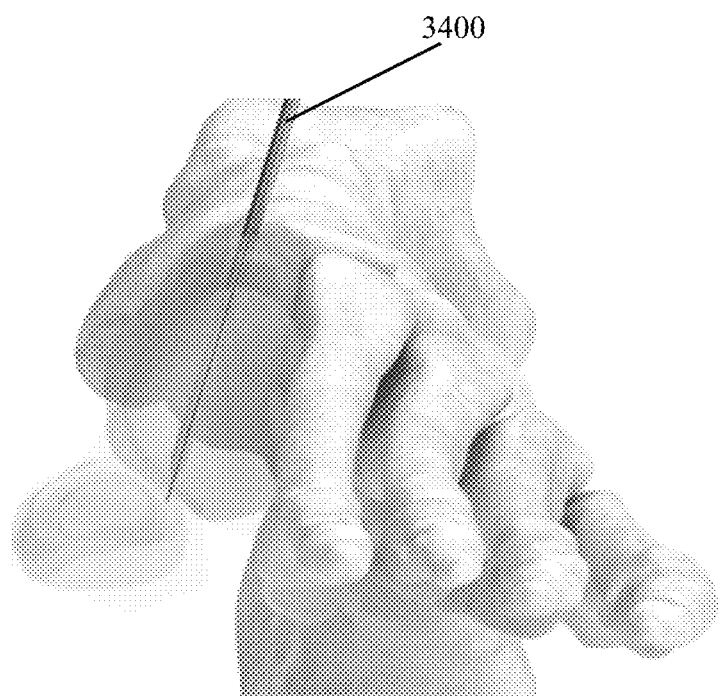
FIG. 19 shows a k-wire in bone after removal of the post drill guide of FIG. 4.

Referring now to FIG. 4, a k-wire 2400 may be placed through bore 2300 of post drill guide 2000 and into the bone. Next, the surgeon may remove post drill guide 2000, leaving k-wire 2400 in the bone as shown in FIG. 19.

Figure 20:
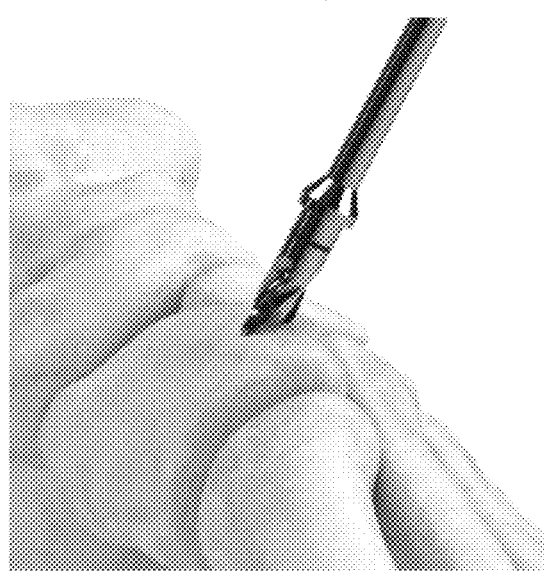
FIG. 20 shows a reamer over the k-wire of FIG. 19.

Referring now to FIGS. 20-21, the surgical technique further comprises inserting a reamer 2405 over k-wire 2400 and drilling until the depth line on the drill bit is at or just below bone surface. As illustrated in FIGS. 22-23, the surgeon next inserts post 1200 and targeting guide 3000 assembly into the previously reamed hole located in the medial cuneiform. The surgeon then fully seats post 1200 into the bone ensuring targeting guide 3000 depth lines are at or just below bone surface.

Figure 24:
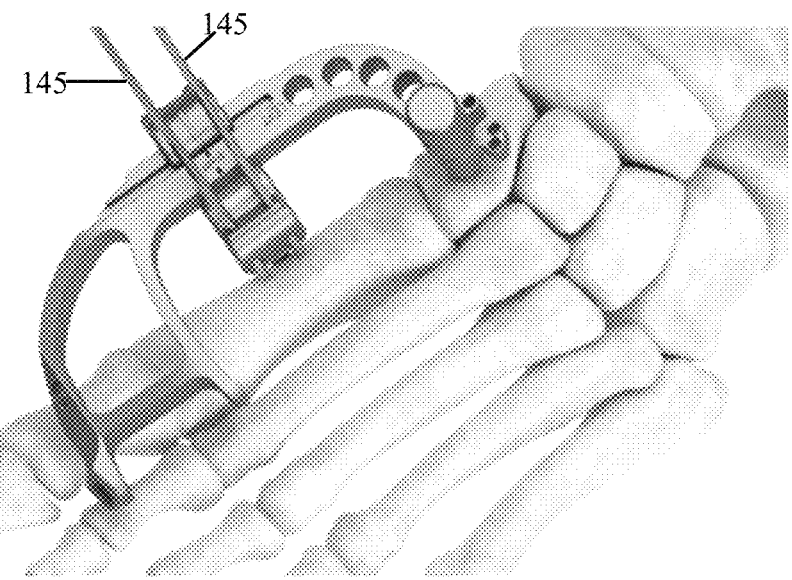
FIG. 24 shows another view of the targeting guide and implant post of FIG. 22 manipulating the metatarsal.

FIG. 24 depicts a surgeon manipulating targeting guide 3000 such that fixture 4000 applies pressure to the metatarsal to correct any frontal plane deformity. Once the metatarsal is rotated to desired location, two k-wires 145 (e.g., two 2 mm k-wires) are placed through bores 3325 of compression-distraction fixture 4000 and into the metatarsal to stabilize the correction. The k-wires could be smooth or threaded. Further a Steinman pin may be substituted for each k-wire.

Figure 25:
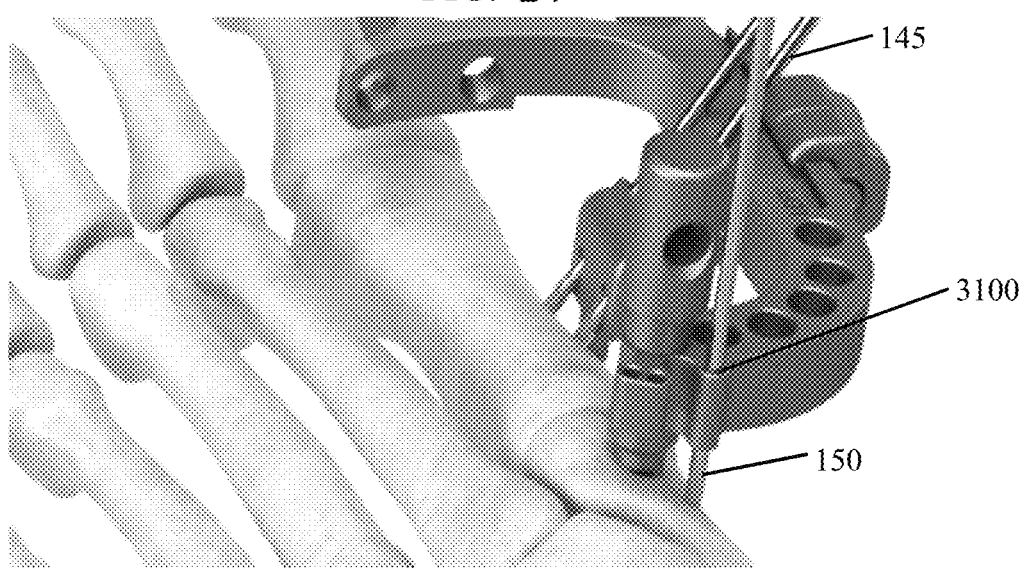
FIG. 25 shows the targeting guide and implant post of FIG. 22 with the wires in the bone manipulating the bone angle.

Referring to FIG. 25, the surgeon may pivot targeting guide 3000 and manipulate the metatarsal to correct a bone angle. Once the metatarsal is in the desired location, the surgeon can lock the correction by inserting a k-wire 150 through a hole 3100 of guide 3000 and into the metatarsal but proximal to post 1200.

Figure 26:
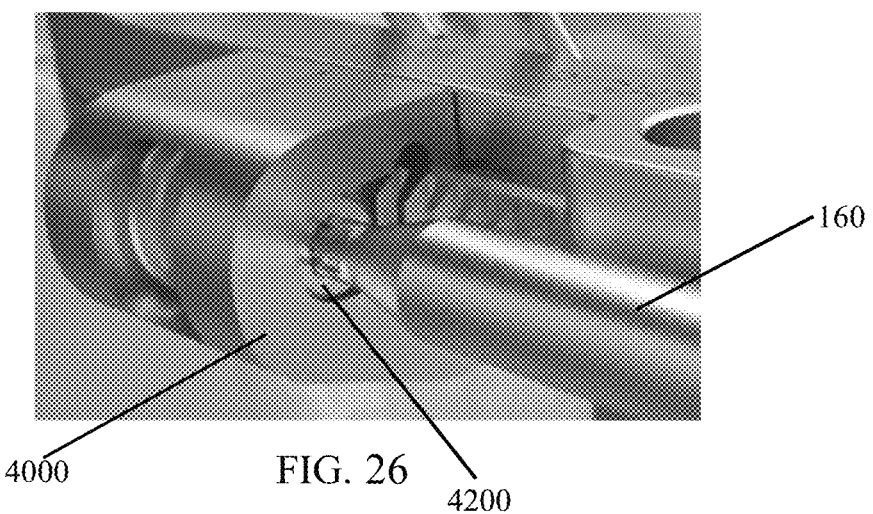
FIG. 26 shows a screwdriver engaging a screw of the compression distraction fixture of FIG. 25.

Referring next to FIG. 26, a driver 160 (e.g., a T10 driver) may be utilized to turn screw 4200 in compression-distraction fixture 4000 counter-clockwise to distract the first tarsometatarsal joint. After desired distraction is achieved, the surgeon may prepare the joint with curettage, microfracture, and other preferred bone preparation methods. Following bone preparation, screw 4200 is turned clockwise to compress the metatarsal to the medial cuneiform.

Figure 27:
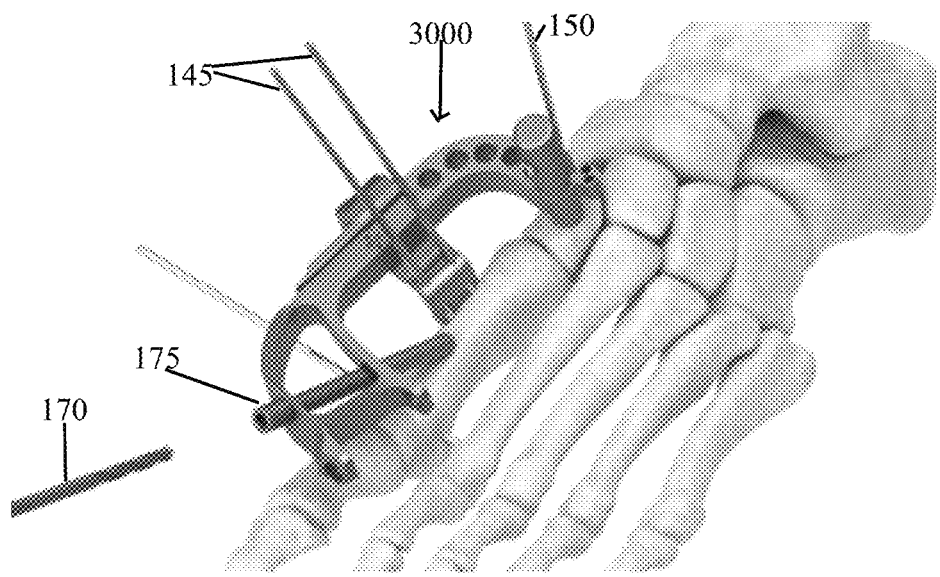
FIG. 27 shows a targeting guide, bushing, and drill bit in accordance with the present invention.
Figure 28:
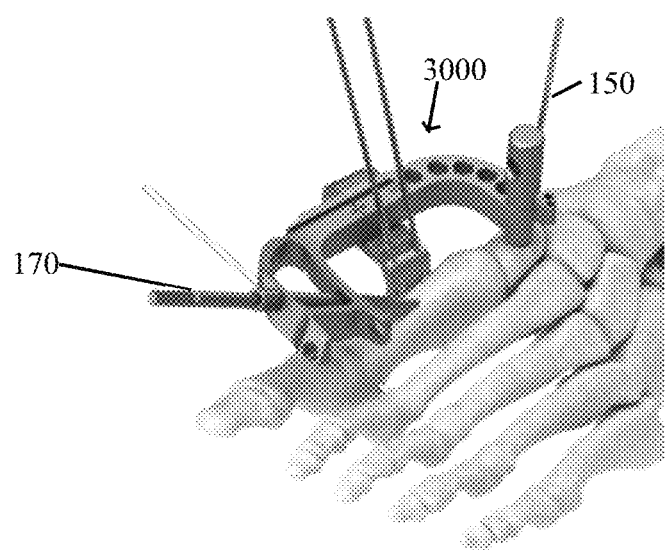
FIG. 28 shows the targeting guide and drill bit of FIG. 27 with the drill bit engaged with the targeting guide.

As depicted in FIGS. 27-28, once desired correction is achieved and secured in compression, the surgeon places a bushing 175 into medial hole 3305 in the targeting guide 3000. The bushing may be chosen to be the longest bushing that will fully seat against guide 3000 without touching the metatarsal.

Figure 29:
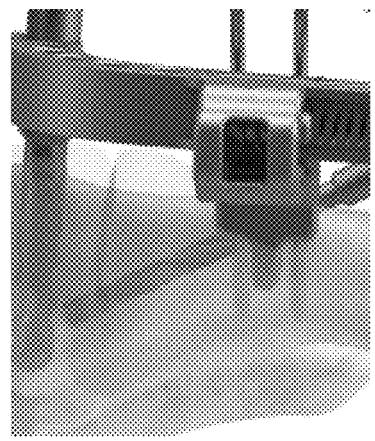
FIG. 29 is a side view showing the drill bit extending toward the post of FIG. 28.

As illustrated in FIGS. 28-29, the surgeon introduces a drill bit 170 (e.g., a 3.6 mm drill bit) into bushing 175 and fully seats drill bit 170 against bushing 175 (up to a step on the drill bit) to ensure that the drill creates a continuous tunnel of an appropriate length to post 1200.

Figure 30:
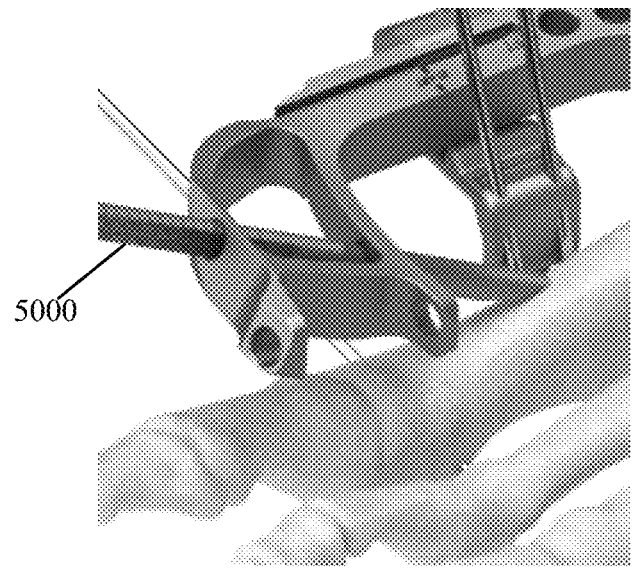
FIG. 30 shows a depth probe engaging a bushing of FIG. 28.
Figure 31:
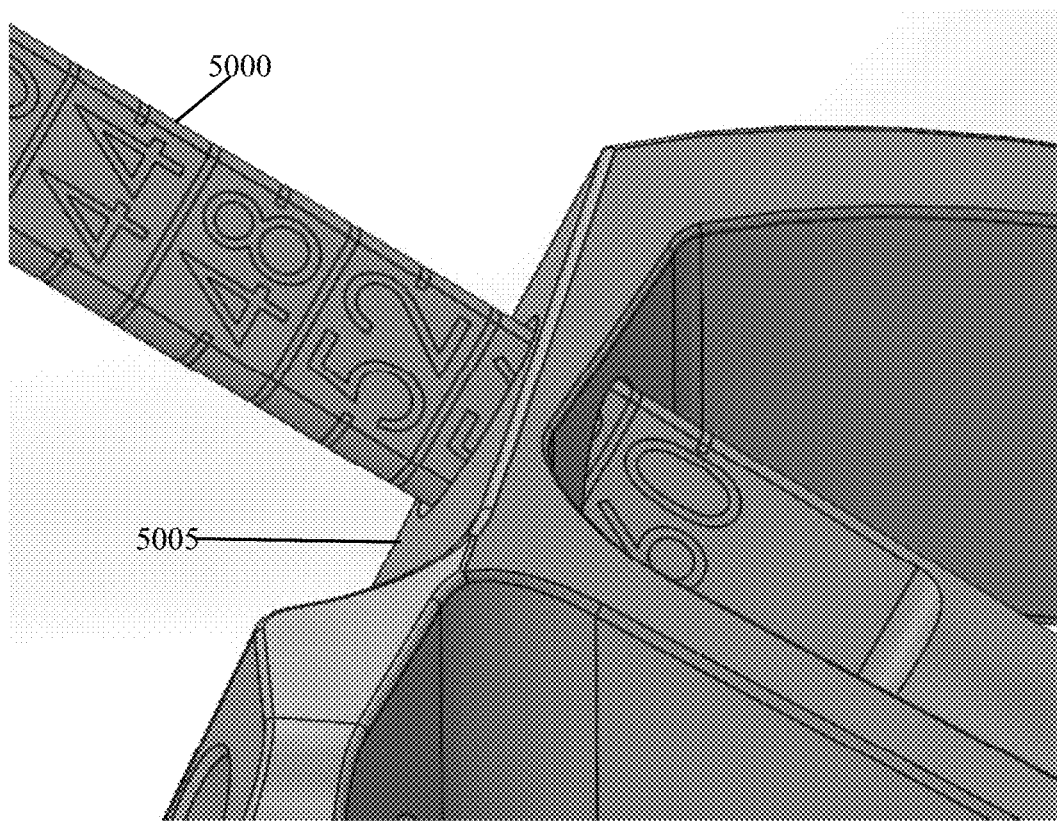
FIG. 31 shows a close-up view of the depth probe of FIG. 30.
Figure 32:
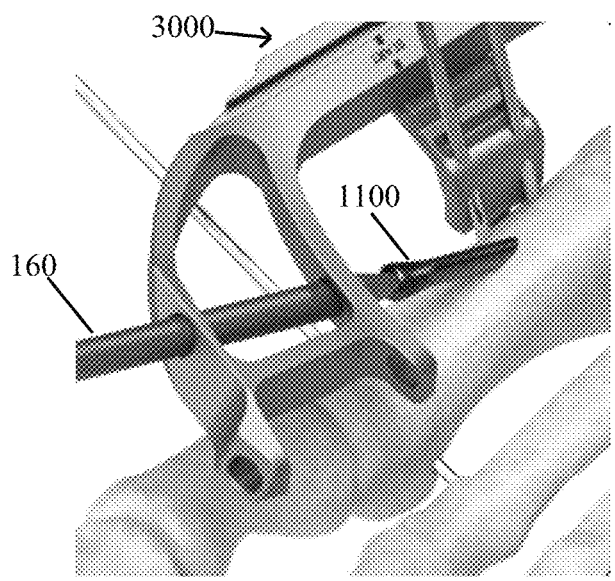
FIG. 32 shows the targeting guide of FIG. 28 with a screw inserted into a tunnel in the bone.
Figure 33:
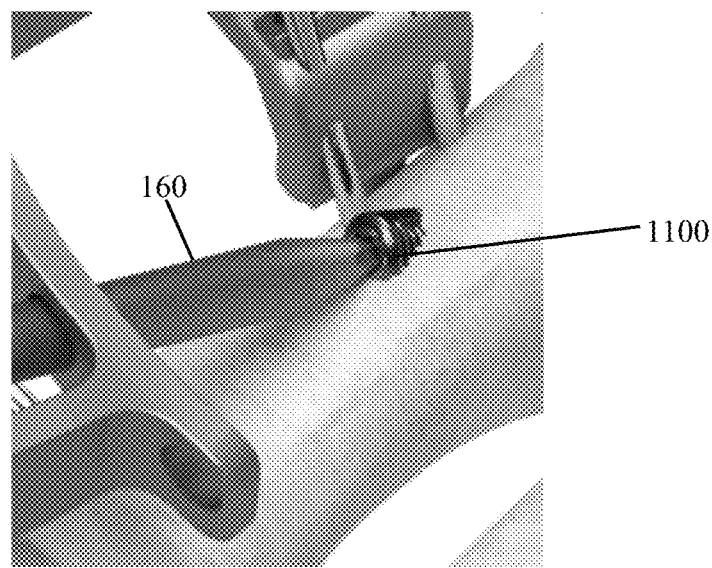
FIG. 33 shows the targeting guide and screw of FIG. 31 with the screw advanced.
Figure 34:
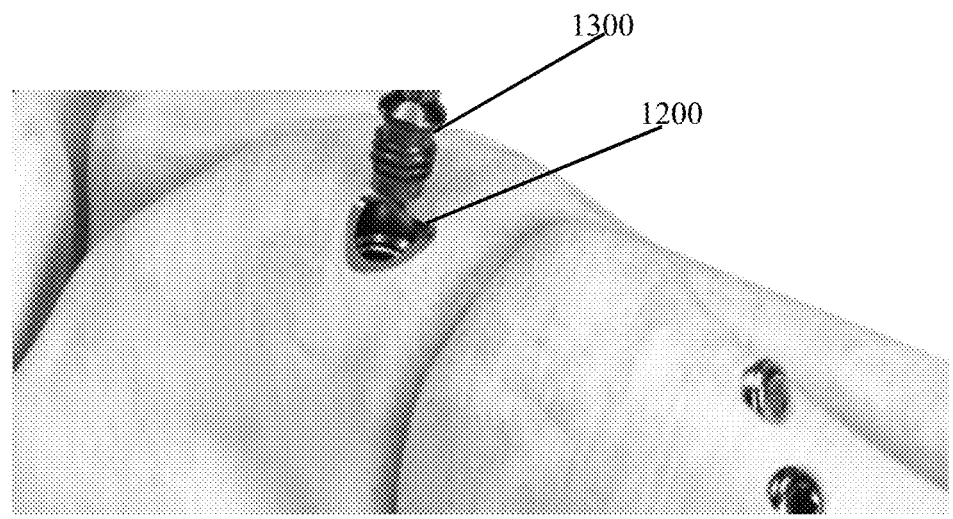
FIG. 34 shows a post plug in accordance with the present invention.

As depicted in FIG. 30, bushing 175 may be removed and a depth measuring probe 5000 may be inserted through a hole (e.g., hole 3305) in targeting guide 3000 and into the tunnel previously created until the probe 5000 contacts bone (i.e., at the end of the tunnel). A measurement may be read at an outside guide surface 5005 (FIG. 31) which correlates with a suggested screw length. Based on measurement, the surgeon selects a screw 1100 and inserts the same through the pre-drilled tunnel until it reaches post 1200 or the rear screw head reaches the bone as depicted in FIG. 32. Then, the surgeon rotationally advances screw 1100 until the desired depth is achieved (FIG. 33). This process is repeated as necessary (FIGS. 32-33). The surgeon may reduce the compression by turning screw 4200 counter-clockwise and removing all three k-wires (e.g., wire 150, wires 145). The surgeon may release post fastener 1500 from post 1200 and remove targeting guide 3000. Once both screws 1100 are locked into post 1200, the surgeon may thread a post screw 1300 into the top of the post (FIG. 34).

The screws described above may be driven by a screwdriver operated by a surgeon. Such a screwdriver may be configured with an alignment feature which includes a cylindrical feature at the tip of the driver, smaller than the feature that generates torque, that inserts into a cylindrical hole feature at the bottom of the screw's drive feature. This alignment feature is important to ensure that the axis of the screw and the axis of the driver are colinear. This prevents the screw from deviating from the drilled tunnel (in soft bone) and missing the holes in the post. The screw is configured to be minimally retained with the driver, such that it need not be held to the driver during insertion (i.e., so it doesn't fall off of the driver).

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

The invention claimed is:

1. An orthopedic instrument assembly for placing an implant into a medial cuneiform of a foot, the assembly comprising:
 a targeting guide;
 a compression-distraction fixture for compressing a joint prior to placement of a joint fixation element, the compression-distraction fixture translatably connected to the targeting guide, the compression-distraction fixture releasably, statically connectable to a first bone of the foot; and
 a post, the post having a generally cylindrical shape and a longitudinal axis, the post comprising a plurality of threaded cylindrical bores disposed through the post at predefined angles relative to the longitudinal axis, the post releasably, statically connectable to the targeting guide such that the targeting guide and the post may rotate around the longitudinal axis.

2. The orthopedic instrument assembly of claim 1 wherein the targeting guide comprises a body having an elongated linear base and a threaded rack disposed along the elongated linear base, and wherein the compression-distraction fixture is translatably connected to the threaded rack.

3. The orthopedic instrument assembly of claim 2 further comprising a transverse screw configured to be inserted through the post into a bone around the longitudinal axis.

4. The assembly of claim 3, wherein the transverse screw has a solid shaft.

5. The assembly of claim 3, wherein the transverse screw comprises a first transverse screw and further comprising a second transverse screw.

6. The assembly of claim 3, wherein a diameter of the post is at least 1.5 times the diameter of the transverse screw.

7. The assembly of claim 3, wherein a diameter of the post is no greater than 2.5 times the diameter of the transverse screw.

8. The assembly of claim 3, wherein a post diameter of the post is from times to 2.5 times a screw diameter of the transverse screw.

9. The assembly of claim 3, wherein the transverse screw is a locking screw.

10. The assembly of claim 3, further comprising an elongated depth probe disposed at a predetermined angle through the targeting guide, the depth probe having a distal tip adapted for contact with a bone.

11. The instrument of claim 2 wherein the compression-distraction fixture comprises a fixture bore receiving a k-wire configured to penetrate into the metatarsal bone to connect the compression-distraction fixture to the metatarsal bone.

12. The instrument of claim 11 wherein the k-wire is aligned by the fixture bore to avoid a remainder of the instrument and any hardware between the instrument and the metatarsal bone.

13. The instrument of claim 2 wherein the compression-distraction fixture is configured to be connected to the metatarsal bone by a connecting member passing through a bore in the fixture and penetrating into the metatarsal bone.

14. The instrument of claim 13 wherein the connecting member comprises a smooth k-wire, a threaded k-wire or a Steinmann pin.

15. The instrument of claim 13 wherein the connecting member is guided into a position by the fixture such that the connecting member avoids any hardware between the instrument and the metatarsal bone.

16. The instrument of claim 13 wherein the connecting member comprises a first elongate connecting member and further comprising a second elongate connecting member, the compression-distraction fixture guiding the first elongate connecting member and the second elongate connecting member at separate angles with respect to a longitudinal axis of the post.

17. The orthopedic instrument assembly of claim 1 further comprising a transverse screw configured to be inserted through the post into a bone around the longitudinal axis.

18. The orthopedic instrument assembly of claim 1 wherein the first bone of the foot comprises a metatarsal bone.

* * * * *

UNITED STATES PATENT AND TRADEMARK OFFICE
CERTIFICATE OF CORRECTION

PATENT NO. : 11,000,327 B2
APPLICATION NO. : 16/221036
DATED : May 11, 2021
INVENTOR(S) : Schlotterback et al.

Page 1 of 1

It is certified that error appears in the above-identified patent and that said Letters Patent is hereby corrected as shown below:

In the Claims

Column 8, Line 51: Claim 8 Delete "from times to 2.5 times" and insert -- from 1.5 times to 2.5 times --

Signed and Sealed this
Sixth Day of July, 2021

Drew Hirshfeld
*Performing the Functions and Duties of the
Under Secretary of Commerce for Intellectual Property and
Director of the United States Patent and Trademark Office*